US010835169B2

(12) United States Patent
Sato et al.

(10) Patent No.: US 10,835,169 B2
(45) Date of Patent: Nov. 17, 2020

(54) BRAIN FUNCTION INDEX COMPUTING DEVICE AND BRAIN FUNCTION INDEX COMPUTING METHOD

(71) Applicants: Hitachi, Ltd., Tokyo (JP); Jichi Medical University, Shimotsuke (JP)

(72) Inventors: Hiroki Sato, Tokyo (JP); Atsushi Maki, Tokyo (JP); Yukifumi Monden, Shimotsuke (JP); Ippeita Dan, Shimotsuke (JP); Masako Nagashima, Shimotsuke (JP); Eiju Watanabe, Shimotsuke (JP); Takanori Yamagata, Shimotsuke (JP)

(73) Assignees: Hitachi, Ltd., Tokyo (JP); Jichi Medical University, Shimotsuke (JP)

( * ) Notice: Subject to any disclaimer, the term of this patent is extended or adjusted under 35 U.S.C. 154(b) by 190 days.

(21) Appl. No.: 15/085,519

(22) Filed: Mar. 30, 2016

(65) Prior Publication Data

US 2016/0287160 A1 Oct. 6, 2016

(30) Foreign Application Priority Data

Mar. 31, 2015 (JP) ................. 2015-072264

(51) Int. Cl.
*G01N 33/48* (2006.01)
*A61B 5/00* (2006.01)
*A61B 5/16* (2006.01)
*A61B 5/1455* (2006.01)
*G06G 7/58* (2006.01)

(52) U.S. Cl.
CPC ........ *A61B 5/4064* (2013.01); *A61B 5/14553* (2013.01); *A61B 5/168* (2013.01); *A61B 5/7282* (2013.01); *A61B 2503/06* (2013.01)

(58) Field of Classification Search
None
See application file for complete search history.

(56) References Cited

U.S. PATENT DOCUMENTS

| 2008/0138777 A1 | 6/2008 | Rapoza et al. |
| 2012/0245443 A1 | 9/2012 | Atsumori et al. |
| 2015/0119731 A1 | 4/2015 | Yasumura et al. |

FOREIGN PATENT DOCUMENTS

| WO | WO 2011/065237 A1 | 6/2011 |
| WO | WO 2013/111746 A1 | 8/2013 |

OTHER PUBLICATIONS

Y. Monden et al., "Right prefrontal activation as a neuro-functional biomarker for monitoring acute effects of methylphenidate in ADHD children: An fNIRS study," NeuroImage: Clinical, vol. 1 (2012), pp. 131-140.

Japanese-language Office Action issued in counterpart Japanese Application No. 2015-072264 dated Apr. 24, 2018 with English translation (four (4) pages).

*Primary Examiner* — Eric S Dejong
(74) *Attorney, Agent, or Firm* — Crowell & Moring LLP

(57) ABSTRACT

Provided is a technique for computing a brain function index for diagnosing a mental disorder at the individual level, which can be applied to even a child around school age. A brain function index computing device includes a brain activity value calculation processing unit configured to calculate from brain activity signals of a subject a first brain activity value of a region including the meddle frontal gyrus (MFG) and a second brain activity value of a region including the inferior frontal gyrus (IFG); and a brain function index calculation processing unit configured to calculate a brain function index associated with a mental disorder using the first brain activity value and the second brain activity value.

14 Claims, 10 Drawing Sheets

Control group

○ Significant active channel

ADHD group

FIG. 9A

The possibility of
ADHD is high.
Detailed examination is
recommended.

FIG. 9B

The possibility of
ADHD is low.

BRAIN FUNCTION INDEX COMPUTING DEVICE AND BRAIN FUNCTION INDEX COMPUTING METHOD

CLAIM OF PRIORITY

The present application claims priority from Japanese patent application JP 2015-72264 filed on Mar. 31, 2015, the content of which is hereby incorporated by reference into this application.

BACKGROUND

Technical Field

The present invention relates to a device and a method for computing a brain function index that is associated with a brain function of a subject.

Background Art

The cardinal symptoms of attention deficit/hyperactivity disorder (ADHD) are defined by the Diagnostic and Statistical Manual of Mental Disorders-IV-TR, DSM-IV-TR based on the inattention, hyperactivity, and impulsivity criteria. The prevalence rate of ADHD is 3 to 7%. Many of such symptoms appear in children of preschool age, and about ⅓ to ½ of them have prolonged symptoms even after they reach puberty or become adults.

In addition, there have been reported cases where secondary disabilities, such as problematic behavior at home or school, may occur if one is raised in an undesirable environment such that he/she is scolded frequently, or experiences repeated troubles in the society, for example. Further, it has been pointed out that as the symptoms of ADHD make daily lives difficult, there is an increased possibility that those with ADHD may have depression or may commit suicide until they become adults after puberty. For the reasons above, early diagnosis and appropriate treatment of ADHD are becoming very important social challenges to be addressed.

Conventionally, ADHD is diagnosed based on an evaluation score of DSM-IV-TR that has been scaled through observation of behavior by parents and teachers. However, evaluation that is based on the observation of behavior strongly depends on the subjective judgments of the parents and the teachers. Thus, establishment of a diagnostic index that is based on more objective biological measurement is demanded. The importance of early diagnosis is common to all diseases. In particular, early diagnosis of ADHD has great advantages in that it can improve the parent-child relationship, arrange a desirable growth environment, prevent problematic behavior from being performed due to a low self-esteem, and prevent sequential occurrence of mental diseases, for example. Further, if there is an objective diagnostic index, it also becomes possible to quantitatively evaluate the effect of improving symptoms through treatment such as medication. Thus, a further improvement of the treatment is expected.

In recent years, research of brain function measurement, which is expected to be applied to a method for objectively diagnosing of ADHD, has been advanced. For example, a difference in the disease state between an ADHD group and a control group (i.e., non-ADHD group) has been clarified using a brain function measurement technique such as functional magnetic resonance imaging (fMRI). However, as many of brain function measurement techniques including fMRI involve strong physical restraint of body motion of a subject, it has been difficult to apply such techniques to patients with ADHD who have symptoms of hyperactivity or impulsivity. For example, in fMRI analyses of children, it has been reported that analysis data of both ADHD children and non-ADHD children have high deviation rates. This is because children move their heads, play around, or carelessly forget rules of a cognitive task, for example, during the fMRI measurement. Thus, for early diagnosis and treatment of ADHD, evaluation of children around school age, which is a suitable age for starting drug therapy, is essential. However, for the reasons above, it has been considered that there is a limitation in applying fMRI that requires strong physical restraint of body motion.

In addition, in the research of ADHD based on fMRI, there is a possibility that a selection bias for only ADHD children with mild symptoms may occur as the data discard rate is high. As described above, a biological measurement index, which can be put into practical use at the clinical site and is useful in distinguishing between those with ADHD and those without ADHD, has not been developed so far.

Meanwhile, an optical brain function measurement technique has started to be used in a variety of fields that includes irradiating a subject with a light beam in the visible to near-infrared region, which has high living body permeability, from the surface of the top of the head and detecting the light beam so as to spectroscopically measure hemodynamic changes in the cerebral cortex. This technique has features such that it is robust to body movement, involves weak physical restraint of body motion, can conduct measurement in an ordinary indoor environment (which includes a bedside measurement), and can perform cognitive tasks face to face. Such features are not present in other brain function measurement methods that require a large-scale and strict measurement environment (e.g., fMRI or positron emission tomography (PET)). Thus, such technique has been used for research of infants to children as well as brain activity measurement performed in an environment that is closer to the everyday environment. Further, utilizing such features, measurement of ADHD children, which has been difficult to perform with other types of modality, has also been advanced (Non-Patent Document 1).

In Non-Patent Document 1, optical brain function measurement is performed using a Go/No-go task that is a representative paradigm characterizing the symptoms of ADHD. The Go/No-go task is a task that teaches a patient to perform an action (e.g., press a button) in response to a specific stimuli (i.e., a Go stimuli), and not perform that action under another specific stimuli (i.e., a No-Go stimuli). The Go/No-go task is suited to measuring, in particular, frontal lobe activity associated with response inhibition in response to a No-Go stimuli. As a result of performing optical brain function measurement based on a Go/No-go task on both an ADHD group and a non-ADHD group, it was found that a region that includes the middle frontal gyrus (MFG) in the right hemisphere at the center was active only in the non-ADHD group. Further, as a result of administering methylphenidate (MPH), which is an ADHD remedy, to the ADHD group, it was found that the right MFG changed such that it exhibited the same activity as those of the non-ADHD group (was normalized).

With respect to data on those without ADHD, it is known that a frontal lobe region that includes the inferior frontal gyrus (IFG) in the right hemisphere at the center becomes active.

RELATED ART DOCUMENTS

Patent Documents

Patent Document 1: WO2013/111746 A

Non-Patent Documents

Non-Patent Document 1: Monden, Y. et al., Right prefrontal activation as a neuro-functional biomarker for monitoring acute effects of methylphenidate in ADHD children: An fNIRS study. NeuroImage:Clinical 1(1), 131-140 (2012).

SUMMARY

However, as the results of Non-Patent Document 1 are based on comparison on the group level, the consistency of measurement results of individuals is unclear. Meanwhile, a technique of Patent Document 1 which is based on a viewpoint of diagnosing individuals, is also known. Patent Document 1 discloses a method for examining a cognitive function associated with ADHD from a response (answer data) to a stroop task that is a type of a cognitive inhibition (interference) task.

Patent Document 1 also illustrates an example in which brain blood flow data obtained through optical brain function measurement is used as in Non-Patent Document 1. However, Patent Document 1 describes that "the brain blood flow data is not always necessary" and fails to describe a specific measurement method, a data analysis method, or an algorithm for estimating a cognitive function.

Further, a stroop task, which utilizes a cognitive conflict when there is a difference between the displayed color of characters and the meaning of the characters (e.g., when characters "green" are displayed in red), is supposed to be presented to a subject who can automatically read characters (i.e., who has learned characters to a certain degree). Thus, it is predicted that the stroop task is difficult to be applied to children of preschool age. The suitable age for applying drug therapy for ADHD is around school age. Thus, a technique that can be applied to children of from around 5 years old is needed.

As appropriate diagnosis and treatment of ADHD children are becoming important social challenges to be addressed, a useful index, which can distinguish between an ADHD child and a non-ADHD child and can be used at the clinical site, is necessary. The results of Non-Patent Document 1 merely show a statistical significant difference between an ADHD children group and a non-ADHD children group that is a comparison target (i.e., control). Thus, an index that can distinguish between an ADHD child and a non-ADHD child at the individual level is needed. Although ADHD has been mainly described above, a similar problem exists for diagnosis of mental disorders other than ADHD for children around school age.

Thus, the present invention provides a technique for computing a brain function index for diagnosing a mental disorder at the individual level, which can be applied to even a child around school age.

For example, in order to solve the aforementioned problems, configurations recited in the claims are adopted. The present application includes a plurality of means for solving the aforementioned problems, but as one of the examples, there is provided a brain function index computing device including a brain activity value calculation processing unit configured to calculate from brain activity signals of a subject a first brain activity value of a region including meddle frontal gyrus (MFG) and a second brain activity value of a region including inferior frontal gyrus (IFG); and a brain function index calculation processing unit configured to calculate a brain function index associated with a mental disorder using the first brain activity value and the second brain activity value.

According to another example, there is provided a method for computing a brain function index using a processor and a memory, including a first step of causing the processor to calculate from brain activity signals of a subject a first brain activity value of a region including meddle frontal gyrus (MFG) and a second brain activity value of a region including inferior frontal gyrus (IFG); and a second step of causing the processor to calculate a brain function index associated with a mental disorder using the first brain activity value and the second brain activity value.

According to the configuration of the present invention, it is possible to obtain a brain function index with which a mental disorder can be diagnosed at the individual level. Such a configuration can be applied to even a child around school age. Further features related to the present invention will become apparent from the description and the accompanying drawings of this specification. Other problems, configurations, and advantages will become apparent from the following description of embodiments.

BRIEF DESCRIPTION OF THE DRAWINGS

FIG. 9A shows an example of a screen that is displayed on a display device in Step 816 of FIG. 8.

FIG. 9B shows an example of a screen that is displayed on the display device in Step 815 of FIG. 8.

DETAILED DESCRIPTION OF THE EMBODIMENT(S)

Hereinafter, embodiments of the preset invention will be described with reference to the accompanying drawings.

Although the drawings show specific embodiments in accordance with the principle of the present invention, such embodiments should be used only for the understanding of the present invention and not for narrowly interpreting the present invention.

The inventors of this application found a novel configuration by conducing concentrated studies from viewpoints that (1) optical brain function measurement can be applied at a low deviation rate to ADHD children at early ages around school age, and (2) there is a possibility that an inhibition function, which is the main disease feature of ADHD, can be visualized, that is, a neuro physiological index that is useful for diagnosing ADHD may be obtained through optical brain function measurement.

The following embodiment relates to a device for calculating a brain function index that reflects an inhibition function and an attention function associated with symptoms of attention deficit/hyperactivity disorder (ADHD). It should be noted that the techniques described below can also be applied to calculation of a brain function index for diagnosing mental disorders other than ADHD.

Figure 1:
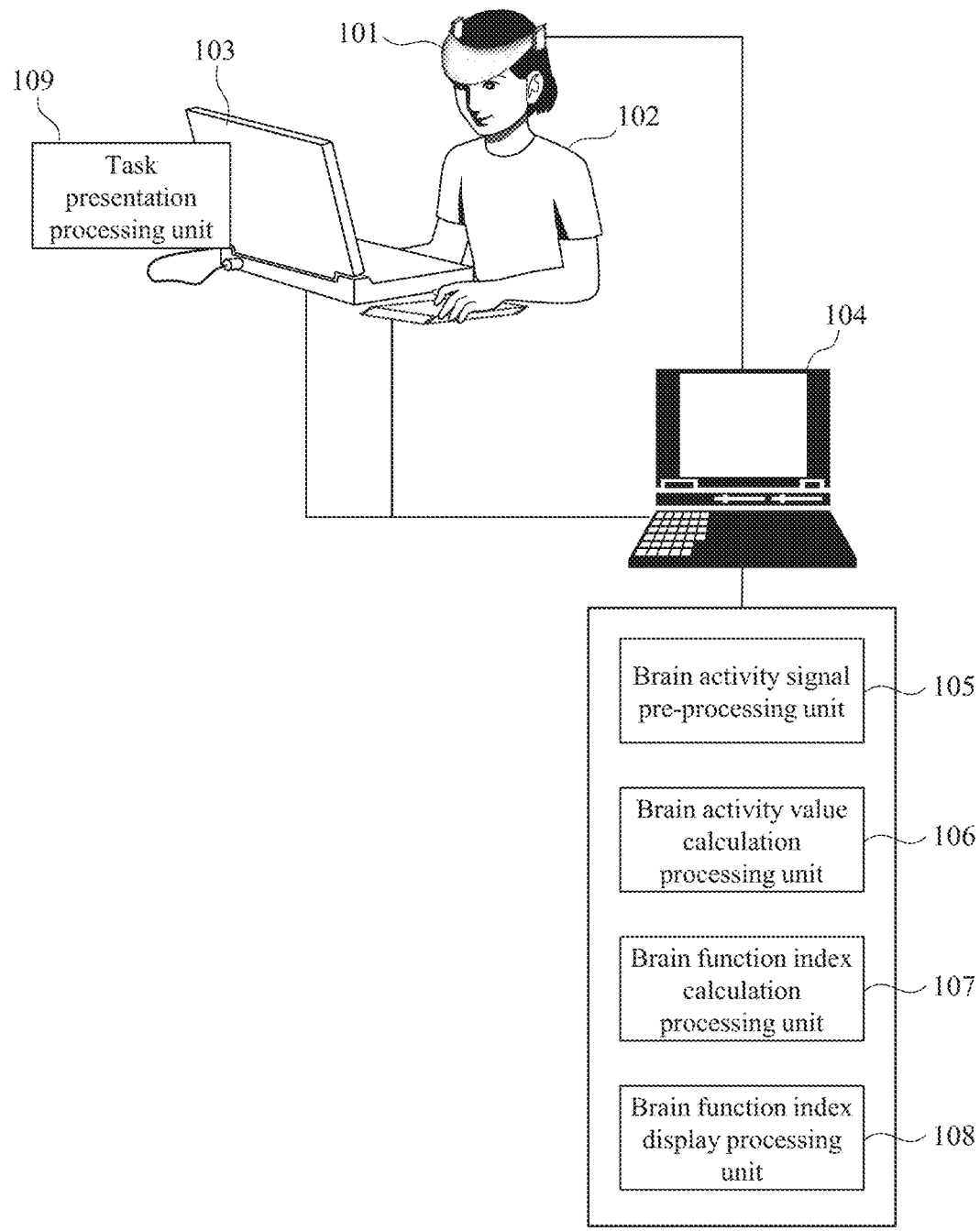
FIG. 1 is a configuration diagram of a brain function index computing system in accordance with an embodiment of the present invention.

FIG. 1 is a configuration diagram of a brain function index computing system in accordance with an embodiment of the present invention. The brain function index computing system includes an optical brain function measuring device 101, a personal computer for presenting tasks (hereinafter referred to as a task-presenting PC) 103, and a personal computer for performing measurement (hereinafter referred to as a measurement PC) 104.

The optical brain function measuring device 101, the task-presenting PC 103, and the measurement PC 104 are connected with wires or wirelessly. Herein, a configuration will be described in which the optical brain function measuring device 101 and the measurement PC 104 are connected, and signals measured with the optical brain function measuring device 101 are directly transmitted to the measurement PC 104. However, the present invention is not limited to such an example. For example, a configuration may be provided in which the optical brain function measuring device 101 and the task-presenting PC 103 are connected, and signals measured with the optical brain function measuring device 101 are once stored in the task-presenting PC 103, and then, data on the signals of the optical brain function measuring device 101 are input to the measurement PC 104 via a network or a storage medium or the like. Thus, any configuration and form are acceptable as long as signals measured with the optical brain function measuring device 101 are provided as input data to the measurement PC 104.

The optical brain function measuring device 101 is mounted on the head of a subject 102. The measurement PC 104 includes a brain activity signal pre-processing unit 105, a brain activity value calculation processing unit 106, a brain function index calculation processing unit 107, and a brain function index display processing unit 108. The task-presenting PC 103 includes a task presentation processing unit 109.

The task-presenting PC 103 displays cognitive tasks on a display device (i.e., display) of the task-presenting PC 103 through the task presentation processing unit 109. The optical brain function measuring device 101 measures signals while the subject 102 is executing a cognitive task on the task-presenting PC 103, and transmits the measured signals to the measurement PC 104. The measurement PC 104 calculates a brain function index by processing signals received from the optical brain function measuring device 101 using the processing units 105 to 108.

Figure 2:
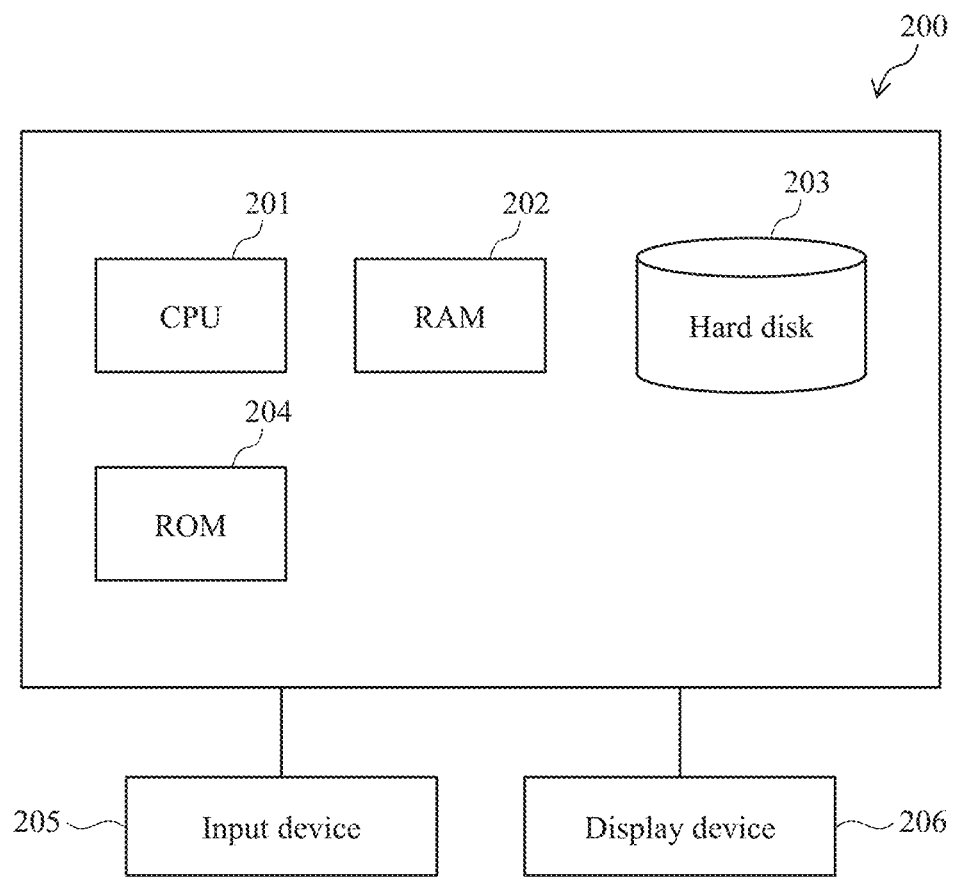
FIG. 2 is a hardware configuration diagram of a personal computer of the brain function index computing system.

FIG. 2 is a hardware configuration diagram of a personal computer (PC) of the brain function index computing system. A PC 200 includes a processor such as a CPU 201, a volatile memory such as a RAM (Random Access Memory) 202, a nonvolatile storage such as a hard disk 203, a ROM 204, an input device 205, and a display device 206. The input device 205 is a keyboard, a mouse, or the like, while the display device 206 is a display or the like.

In this embodiment, the task-presenting PC 103 and the measurement PC 104 can be implemented by causing the PC 200 to read predetermined programs and execute the programs. That is, each of the processing units 105 to 109 of the task-presenting PC 103 and the measurement PC 104 is implemented by storing a program code corresponding to each process in the RAM 202 and causing the CPU to execute each program code.

It should be noted that the task-presenting PC 103 may be any device with which the subject 102 can execute a cognitive task, and may also be implemented by a device other than the PC 200, such as a tablet terminal.

Figure 3:
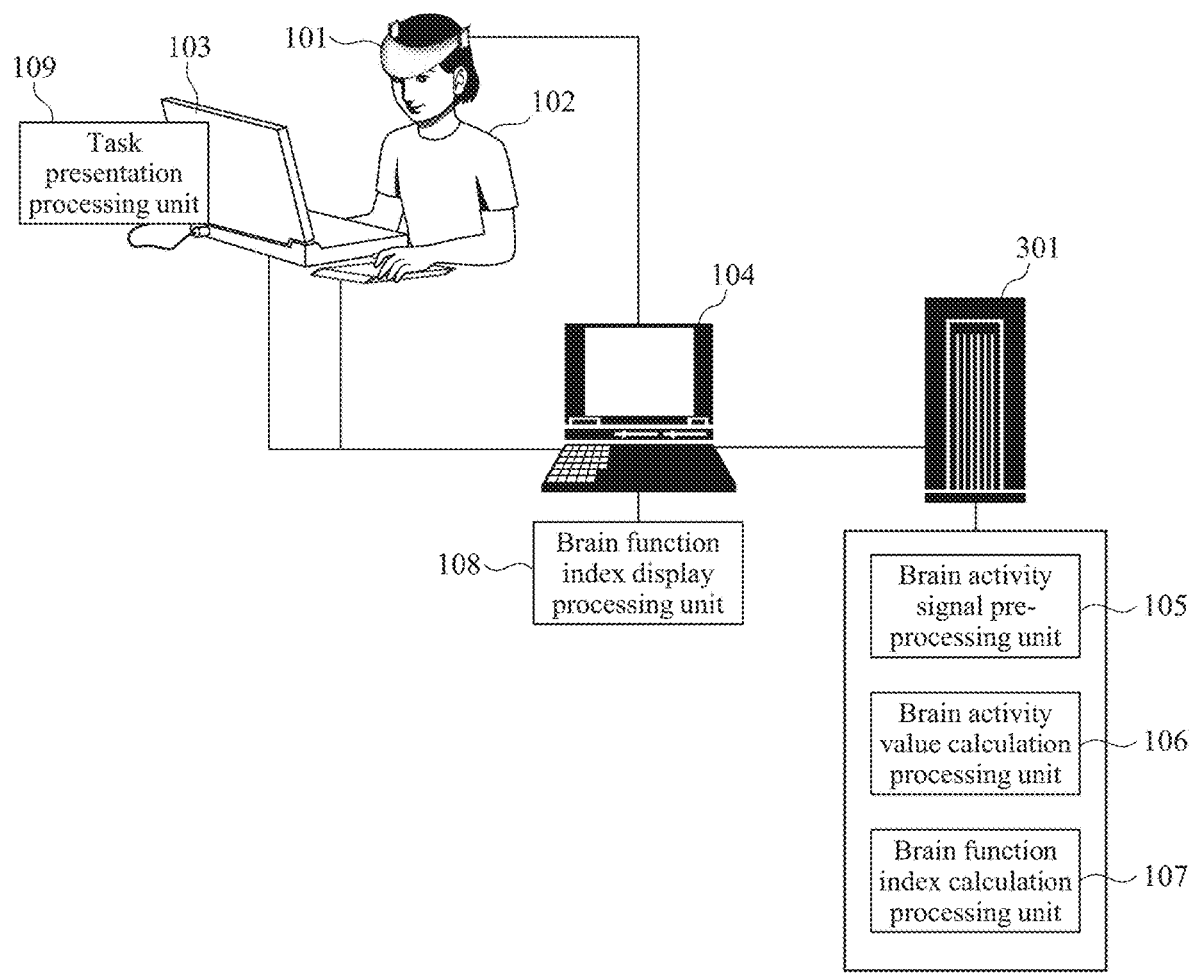
FIG. 3 is a configuration diagram of a brain function index computing system in accordance with another embodiment of the present invention.

Although FIG. 1 shows a configuration in which all of the processes, including acquisition of brain activity signals, pre-processing, and a brain function index displaying process, are performed on the measurement PC 104, the present invention is not limited thereto. For example, the processing units 105 to 108 of the measurement PC 104 may be arranged in a distributed manner on a network. FIG. 3 is a configuration diagram of a brain function index computing system in accordance with another embodiment. The brain function index computing system further includes an analysis server 301. The analysis server 301 includes the brain activity signal pre-processing unit 105, the brain activity value calculation processing unit 106, and the brain function index calculation processing unit 107, while the measurement PC 104 includes the brain function index display processing unit 108.

The measurement PC 104 transmits data on signals acquired from the optical brain function measuring device 101 to the analysis server 301 via a network. The analysis server 301 calculates a brain function index by processing the data on the signals using the brain activity signal pre-processing unit 105, the brain activity value calculation processing unit 106, and the brain function index calculation processing unit 107. The analysis server 301 transmits the calculated brain function index to the measurement PC 104. The measurement PC 104 displays the brain function index on the display device 206 using the brain function index display processing unit 108. It should be noted that the analysis server 301 may also be configured to transmit the calculated brain function index to some display device other than the measurement PC 104. As described above, each of the processing units 105 to 108 may be provided in any component among the body of the optical brain function measuring device 101, the measurement PC 104, a server (i.e., cloud PC) connected via a network, or the like.

Next, a cognitive task that is used to measure a brain function will be described. In this embodiment, the task presentation processing unit 109 of the task-presenting PC 103 executes a process of presenting a cognitive task described below. The subject 102 operates the input device 205 in response to a cognitive task that is displayed on the display device 206. The cognitive task used herein is a Go/No-go task that is a representative cognitive task for checking a response inhibition function. Examples of a cognitive task include a variety of types of tasks, such as a task that requires an attention function and a task that requires a memory function. The cognitive task may be selected in accordance with the type of a mental disorder to be diagnosed.

Figure 4:
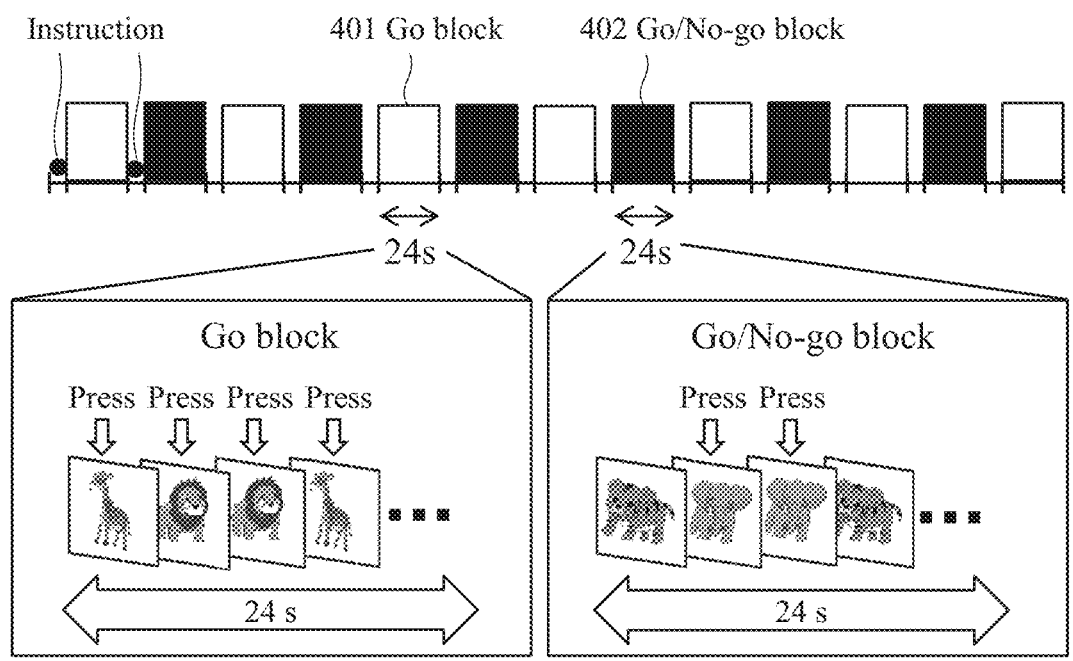
FIG. 4 is a diagram illustrating a Go/No-go task used in an embodiment of the present invention.

FIG. 4 is a diagram illustrating a Go/No-go task. In the example of FIG. 4, Go blocks 401, which are base lines, and Go/No-Go blocks 402, which are targets, are alternately executed for 24 seconds each, and a total of 6 sets of the Go blocks 401 and the Go/No-Go blocks 402 are performed (about 5.5 minutes in total).

As stimuli, color images of four types of animals (i.e., giraffe, elephant, lion, and tiger) were used. Prior to each of the blocks 401 and 402, description of a rule (e.g., in this block, press the button when an elephant is displayed and not press the button when a tiger is displayed) is displayed on the display device 206 for 3 seconds. In the Go block 401 in this embodiment, giraffes and lions are displayed randomly on the display device 206, and the subject is taught to press the button (i.e., input device 205) in response to both the stimuli. Meanwhile, in the Go/No-go block 402, tigers and elephants are displayed randomly on the display device 206, and the subject is taught to press the button only when an elephant is displayed and not press the button when a tiger is displayed.

The subject is taught to press the button as quickly as possible in response to a Go stimulus. Thus, when a tiger of a No-Go stimulus appears, the subject comes close to pressing the button, but he/she should inhibit the action of pressing the button by making efforts. Such function is called an inhibition function, and is known to be mainly controlled by the frontal lobe in the right hemisphere.

Next, each device in FIG. 1 will be described. The optical brain function measuring device 101 is adapted to irradiate a subject with a light beam in the visible to near-infrared region, which has high living body permeability, from the surface of the top of the head and detect the light beam so as to measure hemodynamic changes in the cerebral cortex.

In this example, the optical brain function measuring device 101 measures signals that depend on changes in the blood flow in the brain, using near-infrared spectrophotometry. The optical brain function measuring device 101 has at least two measurement points in the prefrontal region in the right hemisphere of the brain. This embodiment is characterized in that signals, which are obtained from a measurement point corresponding to the middle frontal gyrus in the right hemisphere (hereinafter also referred to as "right MFG") and a measurement point corresponding to the inferior frontal gyrus in the right hemisphere (hereinafter also referred to as "right IFG"), are used as brain activity signals. Thus, it is acceptable as long as the optical brain function measuring device 101 has at least such two measurement points.

It has been reported that there is a relationship between brain activity and the dominant hand. For example, with respect to a left-handed subject 102, it may be preferable to obtain brain activity signals from a measurement point in the MFG in the left hemisphere and a measurement point in the IFG in the left hemisphere. Thus, brain activity signals used in the present invention may be signals that are obtained from a hemisphere of the brain on the same side as the dominant hand of the subject 102.

The optical brain function measuring device 101 has two probe holders corresponding to the right and left hemispheres, respectively. Each probe holder has eight light irradiation probes (i.e., light irradiation portions) and seven photo-detector probes (i.e., photo-detectors). The optical brain function measuring device 101 is configured such that the light irradiation probes and the photo-detector probes are made to contact the head of the subject 102 using ahead set.

The right and left probe holders are mounted symmetrically about the median plane as the midline. At this time, a probe located on the lower forward end of each of the right and left probe holders is adjusted to the position of the supraorbital ridge, and the lower end of the probe is adjusted to the height of the supra-auricular point.

Figure 5A:
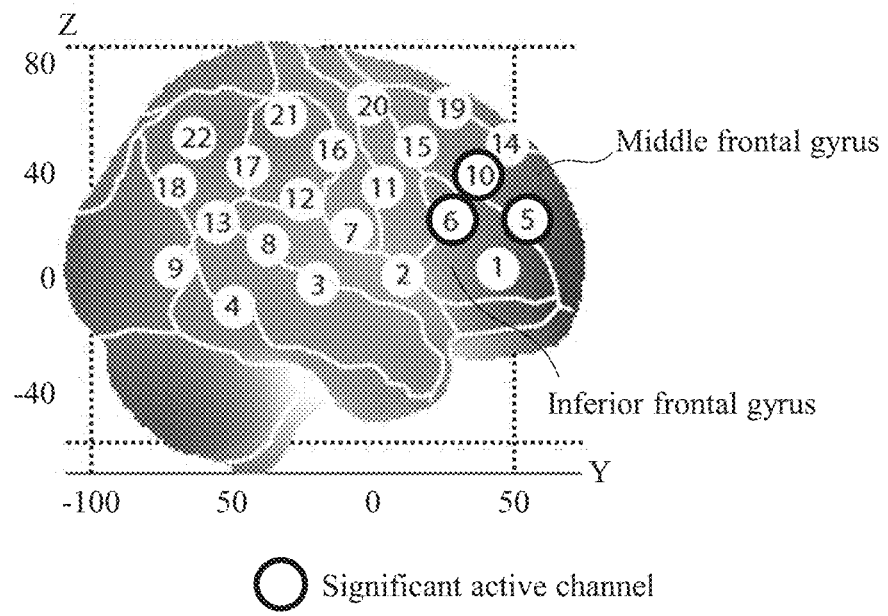
FIG. 5A shows a brain activity map of a control group (i.e., non-ADHD children group)
Figure 5B:
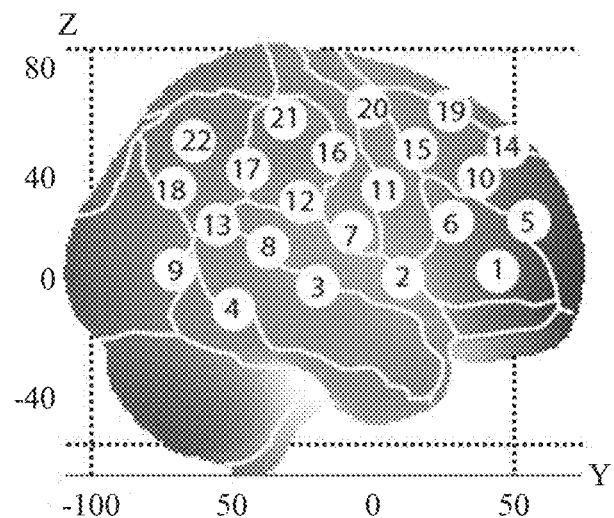
FIG. 5B shows a brain activity map of an ADHD group.

In this embodiment, the eight light irradiation probes and the seven photo-detector probes are arranged in a region covering the frontal region to the temporal region of each of the right and left hemispheres (see FIGS. 5A and 5B). The distance between adjacent probes is 3 cm, and the gap between a light irradiation point and a light detection point is defined as a measurement channel. The optical brain function measuring device 101 measures 22 points including a channel 1 to a channel 22 in each of the right and left cerebral hemispheres (see FIGS. 5A and 5B).

The positions of the measurement channels are virtually arranged on the surface of the head that has been reproduced using the Montreal Neurological Institute (MNI) coordinate system, whereby a brain portion corresponding to each measurement channel can be estimated stochastically. Brain activity signals used in the following example are those obtained from a measurement point (i.e., channel 10) in the right MFG and a measurement point (i.e., channel 6) in the right IFG. It should be noted that the sampling time of the optical brain function measuring device 101 is 0.1 seconds.

Next, brain activity signals used in this embodiment will be described. Each light irradiation probe of the optical brain function measuring device 101 irradiates a subject with a measurement beam in the near-infrared wavelength region. Then, the measurement beam that has passed through and/or has been reflected by the subject is caused to enter one photo-detector probe and is thus detected, so that the intensity of the measurement beam (i.e., the amount of light received) is acquired.

Herein, when the amount of hemoglobin has increased in the activated portion of the brain by reflecting brain activity, the amount of the measurement beam that is absorbed by the hemoglobin is increased correspondingly. Therefore, it is possible to acquire changes in the amount of hemoglobin, which are associated with brain activity, on the basis of the intensity of the acquired measurement beam. Thus, data that is input to the measurement PC 104 from the optical brain function measuring device 101 is time-series data on the intensity of a light beam that has passed through a region of the head including the frontal region and the parietal region, measured with the optical brain function measuring device 101.

The measurement PC 104 calculates relative concentration changes of "oxygenated hemoglobin (Hb)," "deoxygenated Hb," and "sum Hb (i.e., a sum of oxygenated Hb and deoxygenated Hb)" (hereinafter referred to as Hb signals) in the head on the basis of the Lambert-Beer law. It is known that Hb) signals change along with nervous activity. Therefore, such Hb signals are defined as brain activity signals. As a brain activity signal, at least one of an oxygenated Hb signal, a deoxygenated Hb signal, or a sum Hb signal can be used.

A brain activity signal represents a relative change, and is a value representing a variation between the reference period and the brain activity period (i.e., period in which a part of the brain is predicted to be active). Referring to the example in FIG. 4, a brain activity signal represents a difference i.e., variation) between the mean value of signals representing blood amount changes during a given period after an inhibition task is started till it ends (i.e., Go/No-Go block 402) and the mean value of signals representing blood amount changes during a given period before an inhibition task is started (i.e., Go block 401).

It is also possible to acquire brain activity signals for a specific cognitive task by conducting an analysis, taking into consideration information on the type of the task and the presentation timing acquired from the task-presenting PC 103 altogether.

Next, the validity of using brain activity signals from two measurement points, which include the measurement point (i.e., channel 10) in the right MFG and a measurement point (i.e., channel 6) in the right IFG, are shown. When the aforementioned measurement of brain activity signals is conducted on 30 ADHD children and 30 non-ADHD children, which are comparison targets (i.e., controls), brain activity maps such as those shown in FIGS. 5A and 5B are obtained. FIG. 5A shows a brain activity map of the control group (i.e., non-ADHD children group), while FIG. 5B shows a brain activity map of the ADHD group.

This embodiment shows an example in which an oxygenated Hb signal, which has a wide fluctuating range associated with brain activity and has high resistance to noise, is used for an analysis. It is also possible to use other Hb signals (i.e., a deoxygenated Hb signal or a sum Hb signal) as a brain activity signal.

As a result of measuring brain activity signals, significant activity was found in a part of the prefrontal region only in the control group (i.e., non-ADHD children group). The active portions were three channels located in the middle frontal gyrus (MFG) and the inferior frontal gyrus (IFG) (which correspond to the channels 5, 6, and 10 indicated by circles in FIG. 5A). In contrast, no significant active portion was found in the ADHD group. Such analysis results can confirm that activity in the right frontal gyrus that is associated with an inhibition task differs between the ADHD group and the control group.

Figure 6:
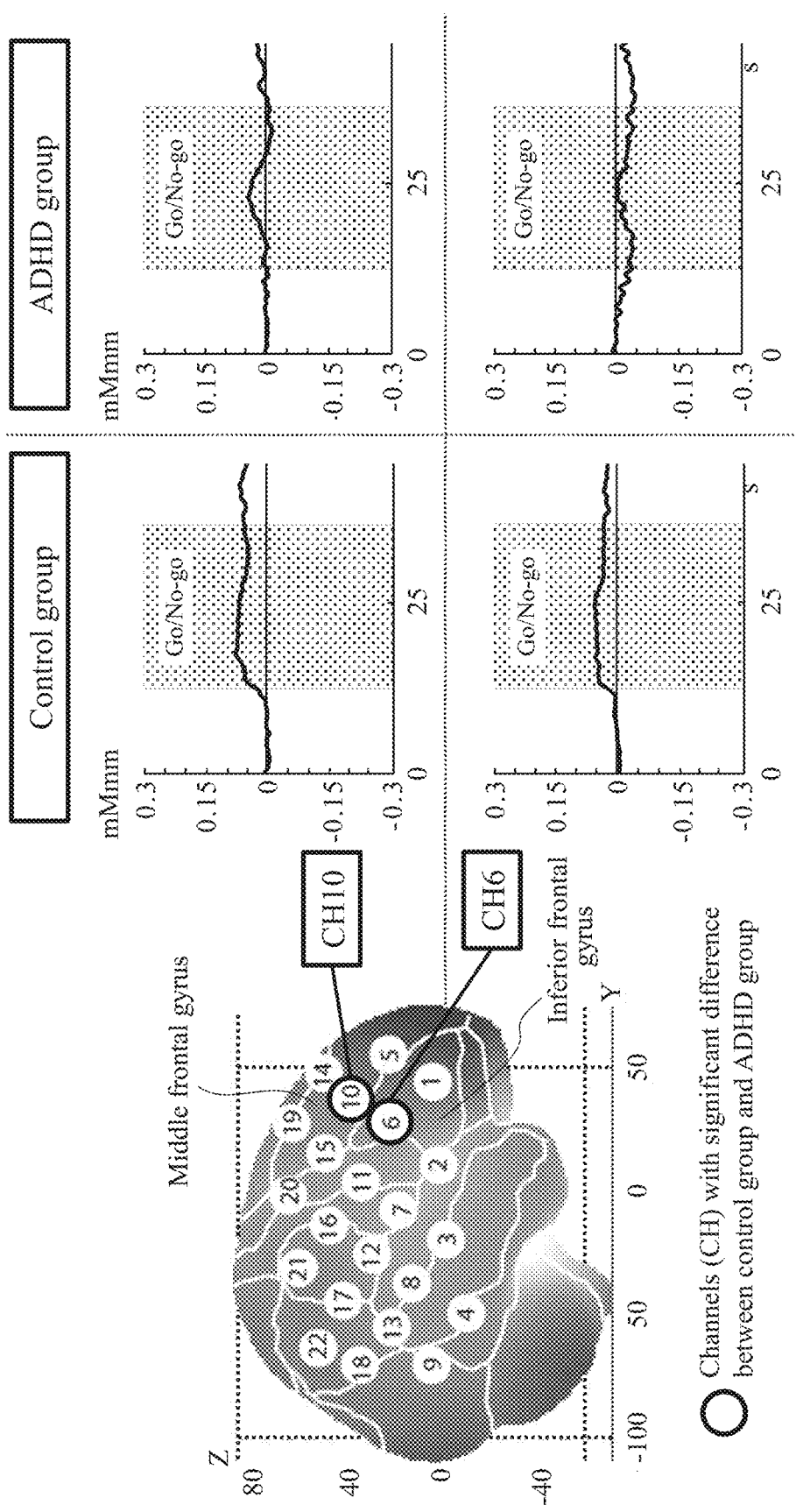
FIG. 6 is a diagram showing results of comparison of brain activity signals obtained from two measurement channels between the control group and the ADHD group.

FIG. 6 is a diagram showing results of comparison of brain activity signals obtained from two measurement channels (i.e., channels 6 and 10) between the control group and the ADHD group. A significant difference was found only in the two channels that are the channel 10 located in the MFG and the channel 6 located in the IFG (i.e., channels indicated by circles in FIG. 6).

In the control group, an increase in the amount of an oxygenated Hb signal associated with a Go/No-Go task was found in the channels 6 and 10, while no significant change was found in the ADHD group. The results indicate that brain functions that characterize the difference between the ADHD children and the non-ADHD children are located locally in the channel 10 in the MFG and the channel 6 in the IFG. It is conventionally considered that the IFG is the main portion that serves an inhibition function. However, as children's IFG are not fully developed, there is a possibility that the MFG is also activated supplementarily.

Based on the above findings, the brain function index computing system in this embodiment calculates a brain function index that is useful for diagnosing ADHD using brain activity signals obtained from both the location of the channel 10 (i.e., a region including the MFG at the center) and the location of the channel 6 (i.e., a region including the IFG at the center). Accordingly, it is possible to provide a brain function index that can distinguish between an ADHD child and a non-ADHD child with high precision and can be used at the clinical site.

Next, each of the processing units 105 to 108 of the measurement PC 104 will be described. The brain activity signal pre-processing unit 105 removes noise from measurement data that has been measured with the optical brain function measuring device 101, for example. The brain activity value calculation processing unit 106 calculates brain activity values from the pre-processed brain activity signals. The brain function index calculation processing unit 107 calculates a brain function index from the brain activity values, and the brain function index display processing unit 108 displays the calculated brain function index on the display device 206.

It should be noted that the measurement PC 104 may perform a process of each of the processing units 105 to 108 using information on the type of a cognitive task and information on the presentation timing. Information on the type of a cognitive task and information on the presentation timing may be acquired from the task-presenting PC 103 or stored in the hard disk 203 of the measurement PC 104 in advance.

Each of the processing units 105 to 108 will be described more specifically. The brain activity signal pre-processing unit 105 performs pre-processing of the measurement data (i.e., the aforementioned time-series data) measured with the optical brain function measuring device 101 to calculate brain activity signals (e.g., pre-processed oxygenated Hb signals).

For example, the brain activity signal pre-processing unit 105 executes the following pro-processing on the measurement data.

(1) Correct the base line using a high-pass filter with a cut-off value of 0.01 Hz.

(2) Apply a low-pass filter with a cut-off value of 0.8 Hz to remove the influence of the heart beat.

(3) Exclude blocks that contain sudden fluctuations from an analysis as such blocks contain motion artifacts.

Alternatively, an analyzing process of extracting only components that are associated with a task using an independent component analysis, for example, is also useful. In that case, the brain activity signal pre-processing unit 105 extracts only components that are associated with a task using information on the type of the task and the presentation timing.

From a viewpoint of removing noise and the like, pre-processing is preferably executed on the measurement data. However, advantageous effects of the present invention can also be obtained even when the measurement PC 104 calculates brain activity signals without executing some or all of the aforementioned pre-processing.

The brain activity value calculation processing unit 106 calculates from an oxygenated Hb signal that has been processed by the brain activity signal pre-processing unit 105 a value (i.e., brain activity value) that represents the magnitude and the significance of a change in the Hb signal associated with a task. The brain activity value calculation processing unit 106 calculates the brain activity value from each of the oxygenated Hb signal corresponding to the MFG and the oxygenated Hb signal corresponding to the IFG.

Herein, the brain activity value is calculated from the signal value of or the waveform information on an oxygenated Hb signal obtained during a given period while an inhibition task is executed, for example. In the example herein, the brain activity value calculation processing unit 106 calculates from the pre-processed oxygenated Hb signals a mean value for an active period of 4 to 24 seconds from the start of a task, as a brain activity value, using information on the presentation timing of the task. That is, the brain activity value calculated herein is a value that represents the mean value of brain activity signals obtained during a given period (for 4 to 24 seconds from the start of a task) after an inhibition task is started till it ends (i.e., Go/No-Go block 402). The reason that data at a time point when 4 or more seconds have elapsed from the start of a task is used is that there is a possibility that a change in the blood flow that is associated with an inhibition task is not likely to appear immediately after the inhibition task is started. Using a mean value as a brain activity value is advantageous in that the influence of noise can be reduced.

The method for calculating a brain activity value is not limited to calculating a mean value for an active period. For example, the maximum value in the period from the start to the end of an inhibition task (i.e., Go/No-Go block 402) may be calculated as a brain activity value. When the maximum value is used, it becomes possible to use the value at a time point when the activity was the highest during execution of an inhibition task for the following calculation of a brain activity index.

Alternatively, it is also possible to use the waveform information on a brain activity signal obtained during a given period after an inhibition task is started till it ends (i.e., Go/No-Go block 402). For example, the measurement PC 104 may store in the hard disk 203 in advance information on a waveform template for a period of from the start to the end of an inhibition task for a non-ADHD child, so that the brain activity value calculation processing unit 106 may calculate the degree of matching between the waveform information on the obtained oxygenated Hb signal and the waveform template. For calculating the degree of matching, a known template matching method may be used. When a waveform template is used, brain activity can be evaluated quantitatively through comparison with a brain activity model. The methods for calculating a brain activity value shown in this embodiment are only exemplary. Thus, specific methods and parameters are not limited to those shown herein.

The brain function index calculation processing unit 107 calculates a brain function index that reflects a cognitive function associated with ADHD, using both the brain activity value corresponding to the MFG and the brain activity value corresponding to the IFG. The brain function index comes in a variety of forms. Herein, whether or not both the brain activity value corresponding to the MFG and the brain activity value corresponding to the IFG are above a given value is determined as the simplest form.

Using the following determination formula (Formula 1) for comparing each brain activity value with a constant (reference value) a, it is determined whether the test result is "positive (i.e., the possibility of ADHD is high)" or "negative (i.e., the possibility of ADHD is low)." Herein, a brain activity value corresponding to the MFG is represented by $V_{MFG}$, and a brain activity value corresponding to the IFG is represented by $V_{IFG}$.

$$V_{MFG} > a \wedge V_{IFG} > a \quad \text{(Formula 1)}$$

Figure 7A:
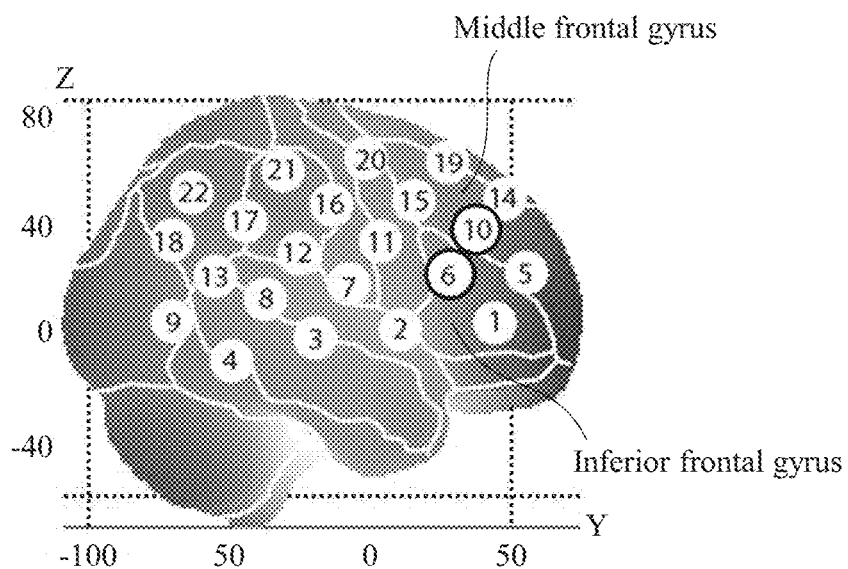
FIG. 7A is a map showing 22 measurement channels including channels 1 to 22 in the right hemisphere of the brain.
Figure 7B:
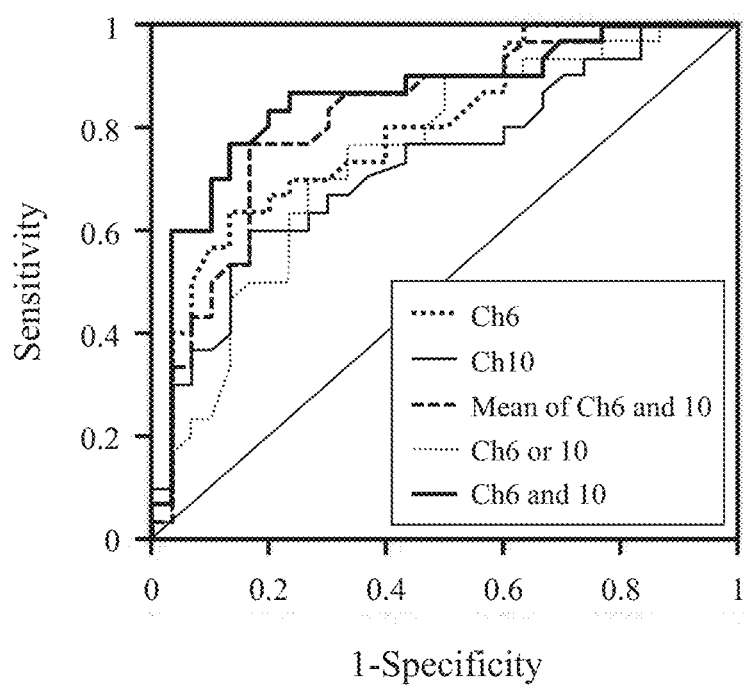
FIG. 7B is a graph showing the results of determining ADHD using brain activity values obtained from channels 6 and/or 10 in FIG. 7A, with the sensitivity and specificity shown on the axes.

FIG. 7A is a map showing 22 measurement channels including channels 1 to 22 in the right hemisphere of the brain. FIG. 7B is a graph showing the results of determining ADHD using the channels 6 and/or 10 in FIG. 7A. The graph in FIG. 7B shows an ROC (receiver operating characteristic) curve that represents how the sensitivity and specificity change, with the constant a sequentially increased from a very low value (i.e., sensitivity=1, specificity=0) up to a very high value (i.e., sensitivity=0, specificity=1).

In FIG. 7B, "Ch6 and 10" shows a result of determination performed based on (Formula 1) above. As a result of determining data in this embodiment by setting the constant a to 0.004 mM·mm and assuming that a case where (Formula 1) is satisfied is "negative" and a case where (Formula 1) is not satisfied is "positive," it was found that a child can be determined to have ADHD under the condition that the sensitivity is 83% and the specificity is 80%. It should be noted that the value of the constant a is not limited to the above value. The constant a may be set in accordance with a variety of conditions such as a method for calculating a brain activity value and a mental disorder to be diagnosed.

"Ch10" shows a result of determination performed on the assumption that a case where the brain activity value corresponding to the MFG (i.e., brain activity value obtained from the channel 10) is above the constant a is "negative" and a case where the brain activity value corresponding to the MFG is not above the constant a is "positive". Meanwhile, "Ch6" is a result of determination performed on the assumption that a case where the brain activity value corresponding to the IFG (i.e., brain activity value obtained from the channel 6) is above the constant a is "negative" and a case where the brain activity value corresponding to the IFG is not above the constant a is "positive."

"Mean of Ch6 and 10" shows a result of determination performed on the assumption that a case where the mean value of the brain activity value corresponding to the MFG (i.e., brain activity value obtained from the channel 10) and the brain activity value corresponding to the IFG (i.e., brain activity value obtained from the channel 6) is above the constant a is "negative" and a case where the mean value is not above the constant a is "positive". Further, "Ch6 or 10" shows a result of determination performed on the assumption that a case where the brain activity value corresponding to the MFG (i.e., brain activity value obtained from the channel 10) or the brain activity value corresponding to the IFG (i.e., brain activity value obtained from the channel 6) is above the constant a is "negative" and a case where both of the brain activity values are not above the constant a is "positive."

As shown in FIG. 7B, when the brain activity value corresponding to the MFG (i.e., Ch 10) or the brain activity value corresponding to the IFG (i.e., Ch 6) is used alone, when the mean value of the two values is used (i.e., the mean of Ch6 and 10), or when whether or not one of the brain activity values is above the constant a is determined (Ch6 or 10), the determination rates are low. This shows that a determination method that uses both the brain activity value corresponding to the MFG and the brain activity value corresponding to the IFG as in (Formula 1) above is preferably used.

Figure 8:
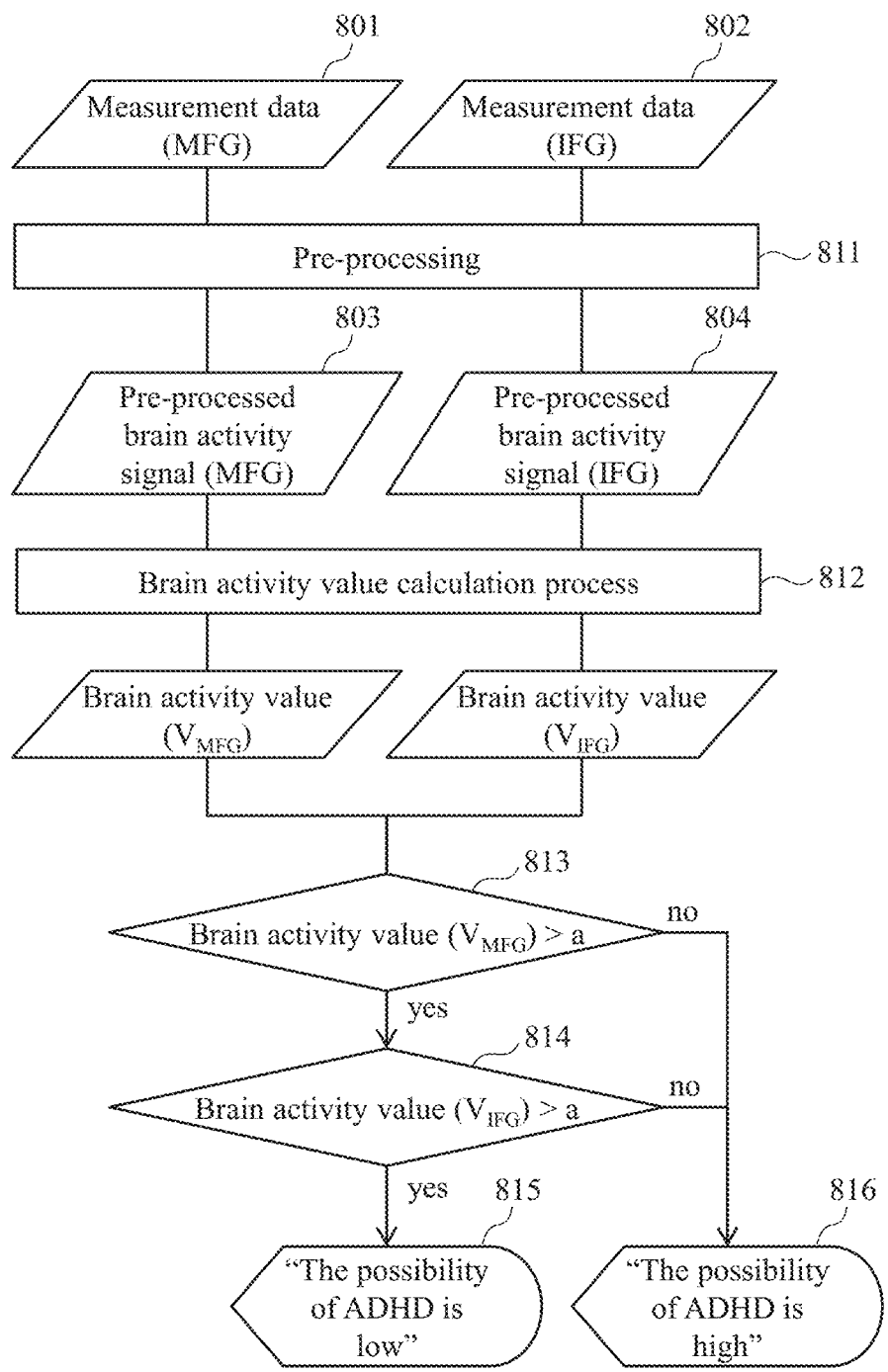
FIG. 8 shows an example of a flowchart showing a process performed by a measurement PC.

FIG. 8 is a flowchart showing a process performed by the measurement PC 104. Although each process in the following description will be described as being performed by one of the functional blocks in FIG. 1 as a subject, each process may also be described as being performed by a processor as a subject because the process is performed when a processor executes a predetermined program using a memory and the like.

The brain activity signal pre-processing unit 105 receives measurement data on the MFG (i.e., measurement data on the channel 10) 801 and measurement data on the IFG (i.e., measurement data on the channel 6) 802 measured with the optical brain function measuring device 101 as input data, and executes pre-processing (811). The brain activity signal pre-processing unit 105 outputs the pre-processed brain activity signal (MFG) 803 and the pre-processed brain activity signal (IFG) 804.

Next, the brain activity value calculation processing unit 106 calculates a brain activity value from each of the brain activity signal (MFG) 803 and the brain activity signal (IFG) 804 (812). Herein, the brain activity value calculation processing unit 106 calculates a brain activity value $V_{MFG}$ first brain activity value) corresponding to the MFG from the brain activity signal (MFG) 803 and a brain activity value $V_{IFG}$ (i.e., second brain activity value) corresponding to the IFG from the brain activity signal (IFG) 804.

Next, the brain function index calculation processing unit 107 determines if the brain activity value $V_{MFG}$ is above the constant a (813). If the determination in Step 813 is Yes, the brain function index calculation processing unit 107 determines if the brain activity value $V_{IFG}$ is above the constant a (814). If the determination in Step 814 is Yes, the brain function index display processing unit 108 displays that "the possibility of ADHD is low" as a diagnostic result on the display device 206 (815). FIG. 9B shows an example of a screen that is displayed on the display device 206 in Step 815. It should be noted that if the determination in either Step 813 or 814 is No, the brain function index display processing unit 108 displays that "the possibility of ADHD is high" as a diagnostic result on the display device 206 (816). FIG. 9A shows an example of a screen that is displayed on the display device 206 in Step 816.

Figure 10:
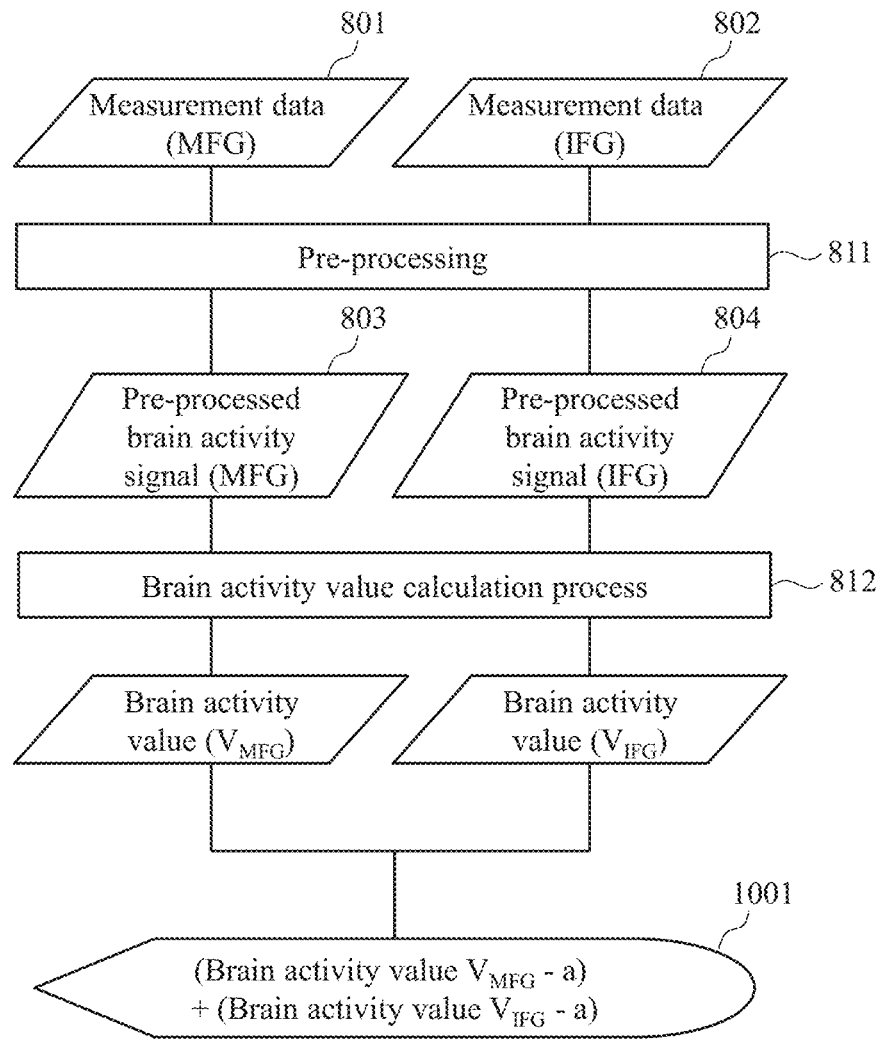
FIG. 10 shows another example of a flowchart showing a process performed by the measurement PC.

FIG. 10 shows another example of a flowchart showing a process performed by the measurement PC 104. The same steps as those in FIG. 8 are denoted by the same reference numerals, and the description thereof will thus be omitted. In the example herein, the brain function index calculation processing unit 107 calculates a score as a brain function index using (Formula 2) below (1001). The brain function index display processing unit 108 displays the calculated score on the display device 206. The score is a value that indicates how much each of the brain activity value $V_{MFG}$ and the brain activity value $V_{IFG}$ is greater than the constant a.

$$\text{Score} = (V_{MFG} - a) + (V_{IFG} - a) \tag{Formula 2}$$

Figure 11:
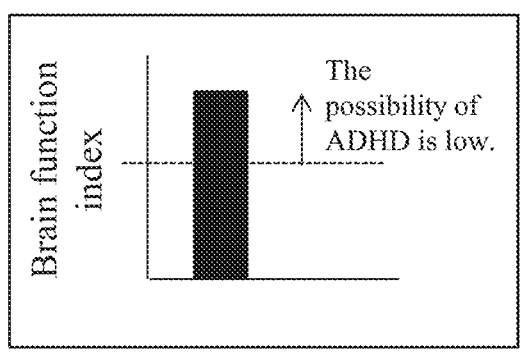
FIG. 11 shows an example of a screen that displays a score calculated in Step 1001 of FIG. 10.

FIG. 11 shows an example of a screen for displaying a score on the display device 206. According to such a configuration, the possibility of ADHD is not represented by a binary value but can be presented as a score. It is also possible to, as shown in FIG. 11, display an indication that the possibility of ADHD is low when a score is above a predetermined threshold (e.g., dotted line in FIG. 11) on the screen. Alternatively, it is also possible to display an indication that the possibility of ADHD is high when a score is not above a predetermined threshold.

The brain function indices described above are only exemplary. Thus, the present invention is not limited thereto. As another example, it is also possible to calculate a score, which serves as a brain function index, from the brain activity value $V_{MFG}$ and the brain activity value $V_{IFG}$, using an arithmetic expression that includes at least one of the four arithmetic operations on the brain activity value $V_{MFG}$ and the brain activity value $V_{IFG}$. For example, a score, which serves as a brain function index, can be calculated using (Formula 3) below.

$$\text{Score} = \frac{V_{MFG} + V_{IFG}}{|V_{MFG} - V_{IFG}|} \tag{Formula 3}$$

From the results in FIG. 7B, it is considered that the difference between the brain activity value corresponding to the MFG and the brain activity value corresponding to the IFG is preferably small, and also that the two brain activity values are preferably high. Thus, using (Formula 3) is considered to be useful for distinguishing between an ADHD child and a non-ADHD child because if the difference between the brain activity value corresponding to the MFG and the brain activity value corresponding to the IFC is large, a low score is obtained.

In addition, although the above example illustrates a case where a brain activity signal corresponding to the right MFG and a brain activity signal corresponding to the right IFG are used, it is also possible to use brain activity signals corresponding to other regions of the brain. For example, it is possible to use brain activity signals obtained from regions other than the MFG or the IFG as reference signals (standard signals) and calculate brain activity signals of the MFG and the IFG from them, and then calculate brain activity values from the brain activity signals. Using signals from other regions as references is advantageous in that it is possible to represent the brain activity states of the MFG and the IFG more effectively.

In this embodiment, frontal lobe activity during execution of a cognitive task, which requires an inhibition function associated with the cardinal symptoms of ADHD, is measured using an optical brain function measurement technique, and then, a brain function index that reflects a frontal lobe function associated with ADHD is calculated using both a brain activity value of the right MFG and a brain activity value of the right IFG. It is considered that the main portion that serves an inhibition function is the IFG. However, as children's IFG is not fully developed, there is a possibility that the MFG is supplementarily activated. According to the above configuration, it is possible to distinguish between an ADHD child and a non-ADHD child with high precision by using activity signals of both the MFG and the IFG.

According to this embodiment, a brain function index that is useful for objectively diagnosing ADHD can be obtained. It was found from data on the comparative experiments of 30 ADHD children and 30 non-ADHD (contrast) children whose sex and ages are matched that when a case where the intensity of a brain activity signal of each of the right MFG and the right IFG is above a given value is assumed to be a negative case of ADHD, it is possible to determine the presence of ADHD under the condition that the sensitivity is 83% and the specificity is 80% (FIG. 7B). The brain function index computing system in this embodiment can be applied to children around school age, which is a suitable age for starting drug therapy for ADHD, and can distinguish between an ADHD child and a non-ADHD child with high precision.

The present invention is not limited to the aforementioned embodiments, and includes a variety of variations. For example, although the aforementioned embodiments have been described in detail to clearly illustrate the present invention, the present invention need not include all of the configurations described in the embodiments. It is possible to replace a part of a configuration of an embodiment with a configuration of another embodiment. In addition, it is also possible to add, to a configuration of an embodiment, a configuration of another embodiment. Further, it is also possible to, for a part of a configuration of each embodiment, add/remove/substitute a configuration of another embodiment.

The process of each of the aforementioned processing units 105 to 109 can also be realized by a program code of software that implements the function of the processing unit. In such a case, a storage medium having recorded thereon the program code is provided to a system or a device, and a computer (or a CPU or a MPU) in the system or the device reads the program code stored in the storage medium. In this case, the program code itself read from the storage medium implements the function of the aforementioned embodiment, and the program code itself and the storage medium having recorded thereon the program code constitute the present invention. As the storage medium for supplying such a program code, for example, a flexible disk, CD-ROM, DVD-ROM, a hard disk, an optical disc, a magneto-optical disc, CD-R, a magnetic tape, a nonvolatile memory card, ROM, or the like is used.

Each of the processes and techniques described above may be implemented substantially by any combination of components without beimg related to any specific device. Further, a variety of types of general-purpose devices can be used. It may be found to be advantageous to construct a dedicated device to execute the processes described above. That is, some of the aforementioned processing units 105 to 109 may be implemented byhardware that uses electronic components such as integrated circuits, for example.

Further, in the aforementioned embodiments, the control lines and information lines represent those that are considered to be necessary for the description, and represent not all control lines and information lines that are necessary for a product. In practice, almost all configurations may be considered to be mutually connected.

DESCRIPTION OF SYMBOLS

101 Optical brain function measuring device
102 Subject
103 Task-presenting PC
104 Measurement PC
105 Brain activity signal pre-processing unit
106 Brain activity value calculation processing unit
107 Brain function index calculation processing unit
108 Brain function index display processing unit
200 PC
201 CPU
202 RAM
203 Hard disk
204 ROM
205 Input device
206 Display device
301 Analysis server

What is claimed is:

1. A mental disorder diagnosis apparatus comprising:
a user interface including a task presentation processor that presents tasks to a subject;
an optical brain function measuring apparatus, including a plurality of brain function sensors attached to the subject, that measures brain activity signals of the subject when the subject executes cognitive tasks;
a processor programmed to execute a program stored in a memory; and
the memory storing the program which, when executed, cause the processor to:
calculate, from the brain activity signals of the subject received from the plurality of brain function sensors attached to the subject, a first brain activity value of a region including middle frontal gyms (MFG) and a second brain activity value of a region including inferior frontal gyms (IFG);
calculate a brain function index of the subject associated with a mental disorder based on the first brain activity value and the second brain activity value of the subject;
determine existence of the mental disorder of the subject based only on the brain function index of the subject; and
output a diagnosis of the mental disorder to a display of a user of the mental disorder diagnosis apparatus to facilitate treatment of the mental disorder;
wherein the optical brain function measuring apparatus is mounted on a subject's head and includes a plurality of light irradiation probes, arranged on right and left hemispheres of the subject's head, that irradiate the subject's head and the plurality of brain function sensors, arranged on the right and left hemispheres of the subject's head adjacent to the plurality of light irradiation probes, that detect the brain activity signals from the subject's head while the subject is executing the cognitive tasks.

2. The mental disorder diagnosis apparatus according to claim 1, wherein the processor is configured to calculate the first brain activity value and the second brain activity value from signal values of or waveform information on brain activity signals obtained during a given period while the subject is executing a cognitive task.

3. The mental disorder diagnosis apparatus according to claim 1, wherein the processor is configured to calculate the brain function index by comparing each of the first brain activity value and the second brain activity value with a reference value.

4. The mental disorder diagnosis apparatus according to claim 1, wherein the processor is configured to calculate the brain function index using an arithmetic expression that includes at least one of four arithmetic operations on the first brain activity value and the second brain activity value.

5. The mental disorder diagnosis apparatus according to claim 1, wherein the brain activity signals are signals obtained from a right hemisphere of a brain or signals obtained from a hemisphere of the brain on the same side as a dominant hand of the subject.

6. The mental disorder diagnosis apparatus according to claim 1, wherein
the brain activity signals are signals obtained while the subject is executing an inhibition task that requires a response inhibition function, and
the brain function index is a diagnostic result or a score that is associated with attention deficit/hyperactivity disorder (ADHD).

7. A method for diagnosing a mental disorder of a subject using a mental disorder diagnosis apparatus including a processor programed to execute a program stored in a memory, the method comprising:
presenting tasks to the subject via a user interface including a task presentation processor that presents tasks to the subject and an optical brain function measuring apparatus, including a plurality of brain function sensors attached to the subject, that measures brain activity signals of the subject when the subject executes cognitive tasks;
causing the processor to calculate, from the brain activity signals of the subject received from a plurality of brain function sensors attached to the subject, a first brain activity value of a region including middle frontal gyms (MFG) and a second brain activity value of a region including inferior frontal gyms (IFG);
causing the processor to calculate a brain function index of the subject associated with the mental disorder based on the first brain activity value and the second brain activity value of the subject;

determining existence of the mental disorder of the subject based only on the brain function index of the subject; and outputting a diagnosis of the mental disorder to a display of a user of the mental disorder diagnosis apparatus to facilitate treatment of the mental disorder;

wherein the optical brain function measuring apparatus is mounted on a subject's head, the optical brain function measuring apparatus including a plurality of light irradiation probes, arranged on right and left hemispheres of the subject's head, that irradiate the subject's head and the plurality of brain function sensors, arranged on the right and left hemispheres of the subject's head adjacent to the plurality of light irradiation probes, that detect the brain activity signals from the subject's head while the subject is executing the cognitive tasks.

8. The method according to claim 7, wherein the first brain activity value and the second brain activity value are calculated from signal values of, or waveform information on, brain activity signals obtained during a given period while the subject is executing a cognitive task.

9. The method according to claim 7, wherein the second step includes calculating the brain function index by comparing each of the first brain activity value and the second brain activity value with a reference value.

10. The method according to claim 7, wherein the second step includes calculating the brain function index using an arithmetic expression that includes at least one of four arithmetic operations on the first brain activity value and the second brain activity value.

11. The method according to claim 7, wherein the brain activity signals are signals obtained from a right hemisphere of a brain or signals obtained from a hemisphere of the brain on the same side as a dominant hand of the subject.

12. The method according to claim 7, wherein the brain activity signals are signals obtained while the subject is executing an inhibition task that requires a response inhibition function, and the brain function index is a diagnostic result or a score that is associated with attention deficit/hyperactivity disorder (ADHD).

13. The mental disorder diagnosis apparatus according to claim 1, wherein the brain activity signals include at least one of an oxygenated hemoglobin signal and a deoxygenated hemoglobin signal.

14. The method according to claim 7, wherein the brain activity signals include at least one of an oxygenated hemoglobin signal and a deoxygenated hemoglobin signal.

* * * * *